(12) United States Patent
Serpe

(10) Patent No.: US 9,759,648 B2
(45) Date of Patent: Sep. 12, 2017

(54) STIMULUS RESPONSIVE POLYMERIC SYSTEM

(71) Applicant: THE GOVERNORS OF THE UNIVERSITY OF ALBERTA, Edmonton (CA)

(72) Inventor: Michael Serpe, Edmonton (CA)

(73) Assignee: The Governors of the University of Alberta, Edmonton, Alberta (CA)

(*) Notice: Subject to any disclaimer, the term of this patent is extended or adjusted under 35 U.S.C. 154(b) by 93 days.

(21) Appl. No.: 14/790,654

(22) Filed: Jul. 2, 2015

(65) Prior Publication Data

US 2016/0033389 A1 Feb. 4, 2016

Related U.S. Application Data

(60) Provisional application No. 62/020,853, filed on Jul. 3, 2014.

(51) Int. Cl.
G01N 19/10 (2006.01)
G01N 5/02 (2006.01)

(52) U.S. Cl.
CPC ............ *G01N 19/10* (2013.01); *G01N 5/025* (2013.01)

(58) Field of Classification Search
CPC ................................ G01N 19/10; G01N 5/025
USPC ............ 73/29.05, 31.01, 31.02, 31.03, 31.05
See application file for complete search history.

(56) References Cited

U.S. PATENT DOCUMENTS

| | | | | |
|---|---|---|---|---|
| 2,249,867 A | * | 7/1941 | Snelling | G01N 31/222 116/206 |
| 2,806,509 A | | 9/1957 | Bozzacco | |
| 3,461,723 A | * | 8/1969 | Thoma | C08L 1/10 73/335.11 |
| 3,671,913 A | * | 6/1972 | Mamiya | G01N 27/121 338/35 |

(Continued)

FOREIGN PATENT DOCUMENTS

| | | |
|---|---|---|
| CA | 2756621 | 4/2013 |
| EP | 0568943 | 11/1993 |

(Continued)

OTHER PUBLICATIONS

Andreas Lendlein et al: Light-Induced Shape-Memory Polymers; Nature; vol. 434; Apr. 14, 2005; p. 879-882.

(Continued)

*Primary Examiner* — Daniel S Larkin
(74) *Attorney, Agent, or Firm* — Anthony R. Lambert

(57) ABSTRACT

Herein, a polymer-based device capable of lifting many times its own mass was fabricated by drying a solution of the polycation poly (diallyldimethyl ammonium chloride) (pDADMAC) on a surface coated with charged poly (N-isopropylacrylamide)-based microgels. Due to strong polymer-polymer and polymer-surface interactions, when the pDADMAC solution dries on the microgel-modified surface, it bends. If the surface is flexible, it curls up into a scroll like structure, that can be opened up at high (ca. 80%) humidity. This process is fully reversible, i.e., if the humidity is decreased, the surface curls back up. This expansion/contraction behavior is capable of lifting relatively large masses, many times its own mass, and can potentially be used as an artificial muscle.

13 Claims, 11 Drawing Sheets

(56) References Cited

U.S. PATENT DOCUMENTS

| | | | | |
|---|---|---|---|---|
| 3,674,439 | A | * | 7/1972 | Hakka .................... G01N 19/10 340/632 |
| 5,150,236 | A | | 9/1992 | Patel |
| 5,672,297 | A | | 9/1997 | Soane |
| 7,168,294 | B2 | * | 1/2007 | Porter .................. G01N 29/022 73/23.2 |
| 7,340,941 | B1 | * | 3/2008 | Fruhberger .......... G01N 29/036 422/88 |
| 7,435,479 | B2 | | 10/2008 | Tsutsui et al. |
| 7,455,903 | B2 | | 11/2008 | Nakayama et al. |
| 7,688,450 | B2 | | 3/2010 | Lei |
| 7,770,433 | B2 | * | 8/2010 | Rothacher .......... B60H 1/00785 250/208.1 |
| 8,110,251 | B2 | | 2/2012 | Markle et al. |
| 8,334,044 | B2 | | 12/2012 | Myung et al. |
| 2004/0050143 | A1 | * | 3/2004 | Hoagland ............ G01N 21/783 73/31.05 |
| 2005/0047968 | A1 | | 3/2005 | Kido et al. |
| 2005/0196532 | A1 | | 9/2005 | Waldrop, III et al. |
| 2006/0261252 | A1 | | 11/2006 | Cole et al. |
| 2007/0248987 | A1 | * | 10/2007 | Imamura .......... G01N 33/54353 435/7.1 |
| 2008/0013159 | A1 | | 1/2008 | Fallahi et al. |
| 2009/0156917 | A1 | | 6/2009 | Martini et al. |
| 2010/0049015 | A1 | | 2/2010 | Martini et al. |
| 2010/0209698 | A1 | | 8/2010 | Kornherr et al. |
| 2013/0110040 | A1 | | 5/2013 | Serpe |
| 2014/0360253 | A1 | * | 12/2014 | Gibson .................. G01N 19/10 73/73 |
| 2016/0033389 | A1 | | 2/2016 | Serpe |

FOREIGN PATENT DOCUMENTS

| | | | |
|---|---|---|---|
| GB | 1061679 | * | 3/1967 |
| GB | 2426333 | * | 11/2006 |

OTHER PUBLICATIONS

David J. Beebe et al: Functional Hydrogel Structures for Autonomous Flow Control Inside Microfluidic Channels; Nature; vol. 404; Apr. 6, 2000; p. 588-590.

T. P. Russell: Surface-Responsive Materials; Science; vol. 297; Aug. 9, 2002; p. 964-967.

Mingming Ma et al: Bio-Inspired Polymer Composite Actuator and Generator Driven by Water Gradients; Science; Jan. 11, 2013; 339(6116; p. 1-9.

Yoshihito Osada et al: Shape Memory in Hydrogels; Nature; vol. 376; Jul. 20, 1995; p. 219-220.

Zi Liang Wu et al: Three-Dimensional Shape Transformations of Hydrogel Sheets Induced by Small-Scale Modulation of Internal Stresses; Article in Nature Communications; Mar. 12, 2013; p. 1-7.

Kai Liu et al: Giant-Amplitude, High-Work Density Microactuators With Phase Transition Actiated Nanolayer Bimorphs; American Chemical Society; 2012; p. 6302-6308.

Xiaobo Zhang et al: Optically-and Thermally-Responsive Programmable Materials Based on Carbon Nanotube-Hydrogel Polymer Composits; American Chemical Society; 2011; p. 3239-3244.

Munenori Yamada et al: Photomobile Polymer Materials: Towards Light-Driven Plastic Motors; Angew.Chem.Int. Ed.; 2008; 47; p. 4986-4988.

Janna C. Nawroth et al: A Tissue-Engineered Jellyfish With Biomimetic Propulsion; Nat Biotechmol; Aug. 2012; p. 792-797.

Yoshinori Takashima et al: Expansion-Contraction of Photoresponsive Artificial Muscle Regulated by Host-Guest Interactions; Nature Communications Article; Dec. 2012; p. 1-8.

Marcio D. Lima et al: Electrically, Chemically, and Photonically Powered Torsional and Tensile Actuation of Hydrid Carbon Nanotube Yarn Muscles; Science; vol. 338; Nov. 16, 2012; p. 928-932.

Chi Wu and Shuiqin Zhou: Laser Light Scattering Study of the Phase Transition of Poly(N-Isopropylacrylamide) in Water.1 Single Chain; American Chemical Society; 1995; p. 8381-8387.

Chi Wu and Xiaohui Wang: Globule-to-Coil Transition of a Single Homopolymer Chain in Solution; The American Physical Society; vol. 80, No. 18; 1998; p. 4092-4094.

Michael J. Serpe et al: Doxorubicin Uptake and Release From Microgel Thiin Films; Biomacromolecules; 2005; 6; 408-143.

Molla R. Islam and Michael J. Serpe: Penetration of Polyelectrolytes Into Charged Poly(N-Isopropylacrylamide) Microgel Layers Confined Between Two Surfaces; American Chemical Society; 2013; p. 1599-1606.

Molla R. Islam and Michael J. Serpe: Polyelectrolyte Mediated Intra and Intermolecular Crosslinkiing in Microgel-Based Etalons for Sensing Protein Concentration in Solution; Cham. Commun.; 2013; 49; p. 2646-2648.

Courtney D. Sorrell and Michael J. Serpe: Reflection Order Selectivity of Color-Tunable Poly (N-Isopropylacrylamide) Microgel Based Etalons; Advanced Materials; 2011; 23; 4088-4092.

Courtney D. Sorrell, Michael J. Serpe: "Glucose Sensitive Poly (N-Isopropylacrylamide) Microgel Based Etalons", Anal Bioanal Chem (2012) 402:2385-2393.

Liang Hu, Michael J. Serpe:"Color Modulation of Spatially Isolated Regions on a Single Poly(N-Isopropylacrylamide) Microgel Based Etalon"; Journal of Materials Chemistry; 2012, 22; p. 8199-8202.

Johnson et al; Detecting Solution pH Changes Using Poly (N-Isopropylacrylamide)-Co-Acrylic Acid Microgel-Based Etalon Modified Quartz Crystal Microbalances; Analytica Chimica Acta 739; 2012; p. 83-88.

Liang Hu, Michael J. Serpe: Color-Tunable Etalons Assembled From Poly (N-Isopropylacrylamide) Based Microgels; Polymers; 2012; 4, p. 134-149.

Sorrell et al. "A "Paint-on" Protocol for the Facile Assembly of Uniform Microgel Coatings for Color Tunable Etalon Fabrication"; American Chemical Society Mater. Interfaces; 2011, 3, p. 1140-1147.

Minghong Yang et al."Optical Fiber Sensors With Fabry-Perot Thin Film Coating as Sensitive Element"; Paper from the 5th International Symposium on Advanced Optical Manufacturing and Testing Technologies, Proc of SPIE; vol. 7659; 2010; p. 1-5.

Xiaobing Li et al.; "Optical Fiber Humidity Sensor With PVDF Thin Film as Sensitive Element"; Proc of SPIE, vol. 7853; p. 1-5, 2010.

Matthew C.D. Carter et al.; "Deswelling Kinetics of Color Tunable Poly N-Isopropylacrylamide) Microgel-Based Etalons"; The Journal of Physical Chemistry B; 2011; 115; p. 14359-14368.

Courtney D. Sorrell et al. Color Tunable Poly (N-Isopropylacrylamide)-Co-Acrylic Acid Microgel-Au Hybrid Assemblies; Advanced Functional Materials; 2011, 21, p. 425-433.

Lian Hu and Michael J. Serpe; Poly (N-Isopropylacrylamide) Microgel-Based Etalons for Optical Sensing; J. Anal Bioanal Techniques; 2012, vol. 3, issue 2; p. 1-4.

T. P. Russell, Surface-responsive materials, Science 2002, 297, 964.

Hoare, T.; Pelton, R. Macromolecules 2004, 37, 2544-2550.

* cited by examiner

| Aspect ratio 1 : 1 (L × W) | Aspect ratio 2 : 1 (L × W) | Aspect ratio 3 : 1 (L × W) | Aspect ratio 4 : 1 (L × W) |
|---|---|---|---|
| 2cm × 2cm | 4cm × 2cm | 6cm × 2cm | 8cm × 2cm |
| 3cm × 3cm | 6cm × 3cm | 9cm × 3cm | 12cm × 3cm |
| 4cm × 4cm | 8cm × 4cm | 12cm × 4cm | 16cm × 4cm |

STIMULUS RESPONSIVE POLYMERIC SYSTEM

CROSS-REFERENCE TO RELATED APPLICATIONS

This application claims the benefit under 35 USC 119(e) of U.S. provisional application No. 62/020,853 filed Jul. 3, 2014.

TECHNICAL FIELD

Stimulus responsive polymeric systems.

BACKGROUND

Polymer-based stimuli responsive polymers and materials have been of considerable interest for many years due to their ability to convert a chemical or physical stimulus into an observable change in a system. Hydrogel-based thin films, assemblies, and particles (microgels and nanogels) have been designed to respond to a variety of stimuli, for a number of potential application in tissue engineering, artificial muscles, valves, and actuators.[1-9] Hydrogels are of particular interest due to their mechanical properties, chemical diversity, and hydration properties, which allows them to interface well with biological systems. Recently, responsive hydrogels and polymer-based thin films has been developed as programmable soft matter or motors by exploiting conformational changes of the polymer that effects the system. [4,6] Of specific interest to the investigation here are responsive polymer-based systems that are able to do work, i.e., lift a mass.[10-12] These systems, often referred to as artificial muscles, have been the subject of intense research due to their potential to control movements in mechanical motors. [10-13]. One of the most well studied responsive polymers to date is poly (N-isopropylacrylamide) (pNIPAm) which shows random coil to globule transition at temperatures below ~32° C.[14,15]

Charged pNIPAm-based microgels have been synthesized and used for various applications.[16-18] By far, the most common chemical functionality added to pNIPAm-based microgels is acrylic acid (AAc). AAc is a weak acid, having a pKa of ~4.25, therefore at pH>4.25 the AAc groups are deprotonated making the microgels negatively charged (polyanionic), while they are neutral at pH<4.25 due to AAc protonation. At high pH the microgels swell due to the charge-charge (Coulombic) repulsion in the microgel's polymer network.

Materials that spontaneously undergo a change in structure, e.g., from a two dimensional (2D) to three dimensional (3D) structure in response to external stimuli have been of great interest as artificial muscles, and for fabricating novel actuators, switches, valves and in robotics.[S1, S2, S3, S4, S5, S6] Various stimuli responsive polymers have been identified, which exhibit responses to electric fields, temperature, light, pH, ionic strength, humidity and/or solvent composition.[S7, S8, S9, S10, S11] Recently, responsive hydrogels and polymer-based films have been used as materials capable of converting chemical or physical energy into mechanical forces, which can lead to macroscopic changes to a material's conformation.[S12] Specifically, temperature responsive poly (N-isopropylacrylamide) (pNIPAm) based hydrogel sheets capable of transforming from a planar state to a 3D structure have been developed by tuning the concentration of monomers and crosslinking density in the hydrogel sheets.[S13] Regions with different polymer content went through differential deformation upon heating allowing the formation of unique 3D structures. Wang et al. recently fabricated near-infrared light-driven hydrogel actuators by interfacing reduced-graphene oxide sheets with protein-based polymers. These hydrogels showed rapid, reversible bending motion at specific positions where near-infrared laser was applied.[S14] Another system composed of a soft poly (butadiene) phase and a hard metal-ligand phase was developed, which exhibited shape-memory properties in response to external stimuli.[S15] In this case, the key component in fulfilling the shape change is the metal-ligand phase which can become soft when exposed to a variety of stimuli (e.g., light, heat, chemicals).

Of recent, several types of humidity responsive polymers have also been used to fabricate actuators. For example, Langer and coworkers[S16] recently developed a polymer composite of rigid polypyrrole (PPy) embedded with a flexible polyol-borate network. PPy can absorb water and change its shape, while the soft polyol-borate network is also sensitive to water, undergoing hydrolysis and reformation of the borate ester crosslinker upon water absorption and desorption, respectively. By breaking and reforming intermolecular hydrogen bonding between PPy and the polyol-borate network and the borate ester within the polyol-borate network upon water sorption and desorption, the film shows expansion and contraction, resulting in the film's rapid and continuous locomotion. In another example, Sun and coworkers developed one bilayer film consisting of a polyelectrolyte multilayer (PEM) film and a layer of UV-cured prepolymer.[S17] The PEM is a film of thermally crosslinked poly (acrylic acid) (PAA)/poly (allylamine hydrochloride) (PAH). The PAA/PAH is able to absorb/desorb water with increasing/decreasing environmental humidity, which resulted in swelling/shrinking of the layer. They fabricated an energetic walking device driven by the powerful humidity responsive PEM.

SUMMARY

In an embodiment, there is disclosed a stimulus responsive device comprising a flexible substrate; a porous intermediate layer attached to the flexible substrate; and a stimulus responsive material bonded to the porous intermediate layer. The porous intermediate layer may comprise a hydrogel. The hydrogel may comprise pNIPAm or polyhydroxyethyl methacrylate. The stimulus responsive material may be responsive to a change in humidity.

The stimulus responsive material may comprise pDADMAC, polyallylamine hydrochloride, polyethylene amine or any positively charged polymer. A metal layer may be provided between the flexible substrate and the porous intermediate layer.

The metal layer may comprise a first metal adjacent to the flexible substrate and a second metal adjacent to the porous intermediate layer. The second metal may comprise Au, Cu, Ni, Al, Ag or Ti. The first metal may comprise for example Ti or Cr. The flexible substrate may comprise a polymer.

The stimulus responsive material may be arranged in strips of respective widths, the respective widths chosen to cause bending at the strips of respective specified angles in response to a stimulus.

In another embodiment, there is disclosed a stimulus responsive device comprising a flexible substrate; and strips of a stimulus responsive material attached to the flexible substrate, in which the strips have respective widths chosen to cause bending at the strips of respective specified angles in response to a stimulus.

3D structures comprising these embodiments are also disclosed.

A method of measuring a stimulus is also provided in which any of the disclosed stimulus responsive devices may be used, and in which the method comprises subjecting the stimulus responsive device to a stimulus to cause a response of the stimulus responsive device; and converting the response to a detectable signal.

These and other aspects of the device and methods are set out in the disclosure and claims.

BRIEF DESCRIPTION OF THE FIGURES

Embodiments will now be described with reference to the figures, in which like reference characters denote like elements, by way of example, and in which:

FIG. 2A shows (left column) bare glass cover slip, (middle column) Au coated glass and (right column) microgel painted on Au coated glass. FIG. 2B shows flexible Au coated substrate with microgels deposited bends and eventually curls upon drying over 8 hours (i-iii).

In FIG. 7A devices were constructed by depositing a single layer of pNIPAm-co-AAc microgels on a flexible plastic substrate (bottom layer) coated with a Au/Cr layer. A pH 6.5 solution of pDADMAC was subsequently added onto the microgel layer and dried. At this pH, there are strong electrostatic interactions between the negatively charged microgels and the positively charged pDADMAC. In FIG. 7B when the pDADMAC layer dries it contracts, and since there are strong electrostatic interactions between the microgels and pDADMAC layers, and the microgels are strongly bound to the Au/plastic layer, the whole device bends as the pDADMAC layer contracts. If the environmental humidity is increased, the pDADMAC layer resolvates, and the device unbends. This bending/unbending mechanism is completely reversible over many cycles.

FIG. 8A shows a detailed view of the device showing the stress generated in the upper layer (Fc), which leads to device bending. The device is considered to be two separate layers, the top layer defined by the pDADMAC-microgel layer and the bottom layer defined by the Au/Cr-coated plastic substrate. FIG. 8B shows a single portion of the device in FIG. 8A. The dashed line represents the initial state of the two layers, while the solid line represents the final state after bending is complete. F1i are the stresses at different points on the Au-plastic substrate, while F2j are the stresses at different points on the microgel-pDADMAC layer. d1 is the thickness of Au-plastic substrate, while d2 is the thickness of the microgel-pDADMAC layer. θ is microscopic bending angle. The blue vectors (force vectors in upper layer) represent the contraction forces in the microgel-pDADMAC layer, while the red vectors (force vectors in lower layer) represent the restoring forces in the Au-substrate layer after the bending is complete.

FIG. 9A is a photograph of a device with dimensions of 3 cm×9 cm before bending. FIG. 9B shows devices of different aspect ratio and dimensions after bending. As can be seen, the devices form different 3D structures after bending dependent on the aspect ratio and size of the devices. L represents the length of the device, while W is the width.

DETAILED DESCRIPTION

Immaterial modifications may be made to the embodiments described here without departing from what is covered by the claims.

Figure 1:
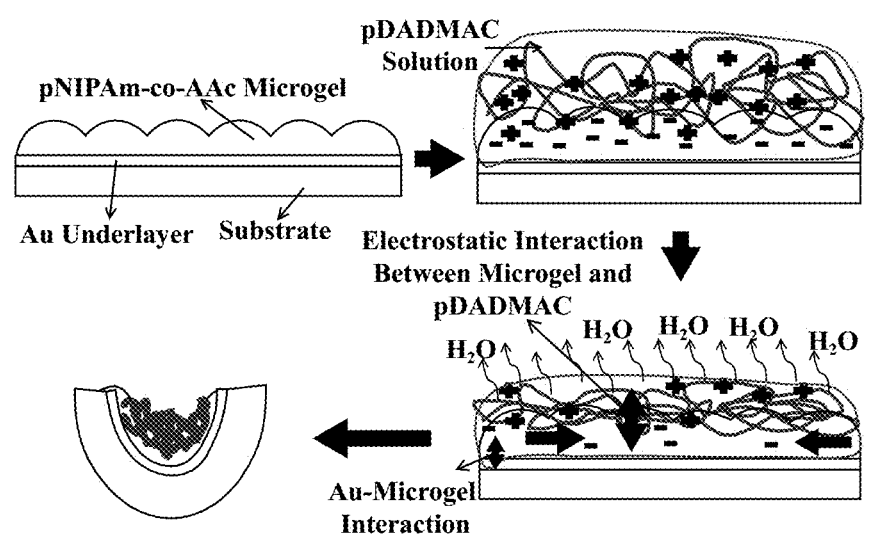
FIG. 1 shows a flexible plastic substrate (transparency film) coated with a Au/Cr layer. Cr acts as an adhesion layer such that the Au adheres to the plastic. PNIPAm-co-AAc microgels were formed on this substrate to yield a monolithic monolayer of microgels on the Au. Addition of pDADMAC solution renders the pNIPAm-co-AAc microgel negatively charged due to the deprotonation of AAc moieties in the microgel initiating the electrostatic interaction between the microgels and polyelectrolyte. Upon drying the pDADMAC layer contracts bending the substrate due to the strong interactions between the microgels and pDADMAC and the microgels and Au.

In this submission we present a pNIPAm microgel-based device that is able to do work, and lift masses many times the device's mass, in response to simple changes in the humidity of its environment. The device is constructed by depositing a monolayer of poly (N-isopropylacrylamide)-co-acrylic acid, pNIPAm-co-AAc microgels on a Au coated substrate. Once deposited, the microgels form a homogenous layer, with the thickness defined by their solution phase diameter. The pNIPAm-co-AAc microgels used here had a solution diameter of 1548±69 nm (measured via differential interference contrast microscopy); the films typically have a thickness of ~0.5 the solution diameter.[19] Subsequently, a solution containing oppositely charged poly (diallyldimethylammonium chloride), pDADMAC is added to the microgel-coated substrate, and allowed to dry. The pDADMAC solution had a pH of 6.55, which rendered the microgel layer polyanionic. The pDADMAC layer contracts when it dries, due to water evaporation enhancing hydrophobic interactions between the pDADMAC chains. Since the electrostatic interactions between pDADMAC and the microgels, and the microgels and the Au, are strong, the substrate bends when the polymer dries as shown in FIG. 1.

Figure 2A:
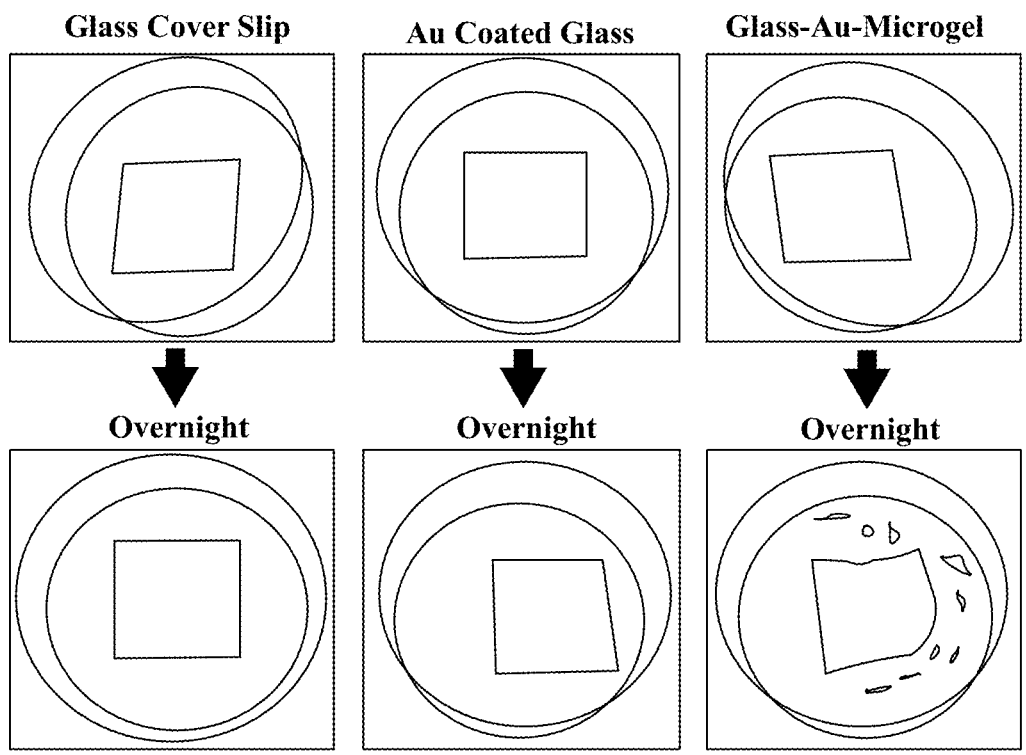
FIG. 2A and FIG. 2B show electrostatic interaction and pDADMAC drying mediated substrate bending. In each case, a fixed amount of pDADMAC solution was added and dried at ambient condition.
Figure 2B:
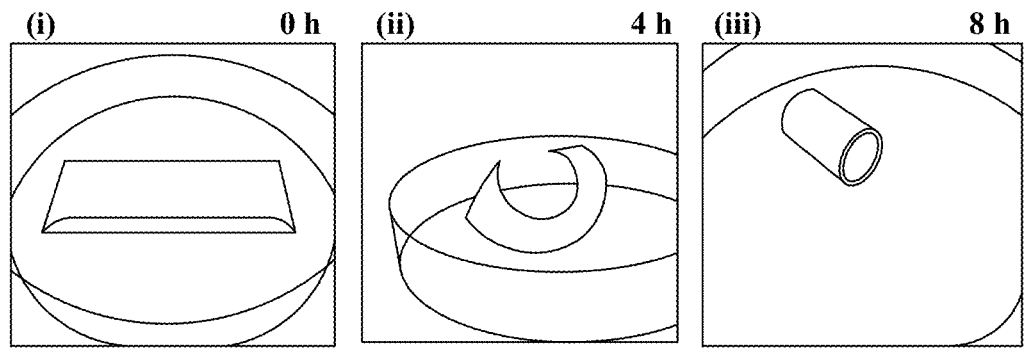

When this process is conducted using standard microscope glass coverslips as the substrate, the bending forces are so strong that the coverslip is shattered. This is shown in FIG. 2A along with the results for control experiments conducted by drying the pDADMAC solution of bare glass and unmodified Au coated glass substrates. As seen in FIG. 2A, when the pDADMAC solution is dried on Au coated glass substrate, with microgels painted on the Au, the glass substrate bends so much that the glass shatters. This was repeated many times, which showed that 80% of the Au coated microgel painted substrates shattered after drying. When the same experiment is conducted on a bare glass substrate, there is no bending observed, while slight bending, and even occasional substrate cracking (~20% of samples) takes place on Au coated glass substrates without microgels present. FIG. 2B shows that when a microgel modified, Au coated plastic substrate (simple transparency slide) in exposed to pDADMAC, and the pDADMAC solution is allowed to dry, the plastic substrate can curl up significantly, into a tight scroll structure. In all the cases above, we hypothesize that the microgels serve as a "glue" that allows the contraction of the pDADMAC layer to be translated to the substrate below. That is, our previous studies have shown that the microgel-Au interaction is extremely strong. Furthermore, we have shown that there are multiple, electrostatic interactions between pDADMAC and the charged microgels.[17] Therefore, the pDADMAC layer contraction upon drying can be translated to the solid substrate through its interaction with the microgels, and the microgels to the Au-coated surface, pulling the sides of the substrate up. Depositing Cr as an adhesion layer between the Au and the substrate strengthens the Au-substrate bond. Drying pDADMAC on a Au-coated substrate without the microgels present does not yield a strong enough bond to the surface to allow for consistent substrate bending/breaking. Similarly, simply drying microgels on a surface does not bend the substrate because when the microgels dry, there are no long-range interactions between them, hence they dry "locally" without long-range deformations that are translated to the substrate.

Figure 3:
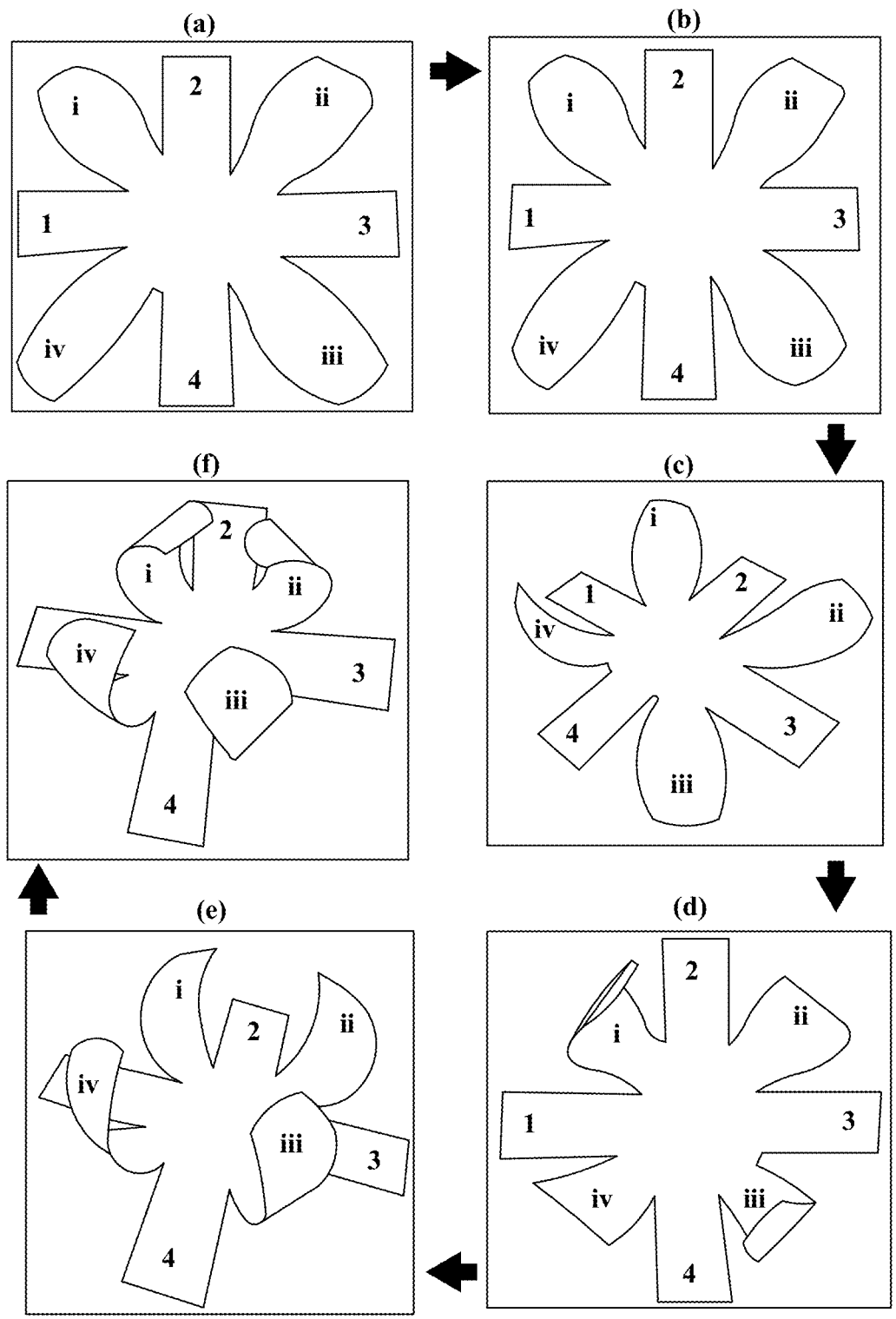
FIG. 3, with plates (a) to (f), shows a specially cut Au coated plastic substrate, with the Au containing pNIPAm-based microgels. Arms i-iv were exposed to the pDADMAC solution while Arms 1-4 were exposed to the PSS solution. The arms that were exposed to pDADMAC clearly bend upon solution drying, while the PSS arms are unresponsive to drying. Drying of the pDADMAC solution took place over 6 hours. After this time, FIG. 3, plate (e), shows the PSS solution was added to the arms and allowed to dry overnight.

To further prove our hypothesis—that it is the electrostatic interactions between the microgels and the pDADMAC that is leading to the observed bending, we designed a flexible substrate with numerous arms. The arms were coated with Au and painted with pNIPAm-co-AAc microgels and alternate arms were exposed to the same pDADMAC solution used above while keeping the other arms empty. As can be seen in FIG. 3, the arms exposed to the pDADMAC solution curl up. When the empty arms were exposed to polyanionic poly (sodium 4-styrenesulfonate) (PSS) solution (20%) and dried at ambient condition did not bend at all. This proves that the polyanionic PSS deposited on the polyanionic microgels cannot yield the necessary interactions with the microgels bound to the Au coated substrate to bend the plastic substrate. Furthermore, this experiment shows that by controlling the shape of the flexible substrate, we are able to devise complex constructs, in this case a "hand"

Figure 4:
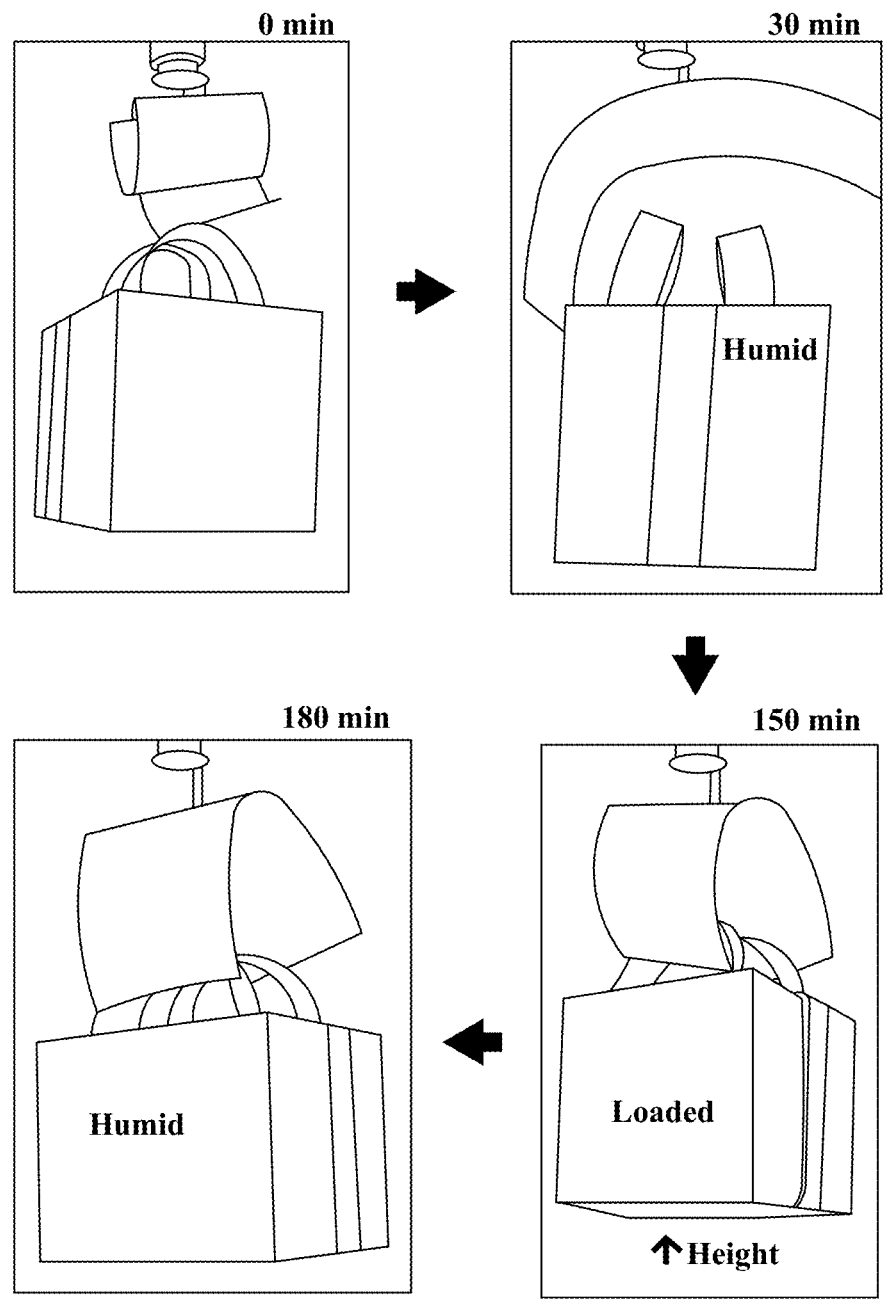
FIG. 4 shows (left) curled substrate hung from a string into a humidity chamber. The humidity of the environment was then increased to 80%, and the device uncurled, which was then lowered close to a box. The humidity was reduced to 10% and the substrate recurled, grasping the box. While maintaining this humidity, the box was lifted off the chamber surface. A subsequent increase in the humidity allowed the device to reopen, and drop the box. The total time of the experiment was ~3 h from left to right. Here, the masses of the device and the box were 0.2 g and 4.8 g respectively.

If our above hypothesis is correct, and the bending of the substrates is a result of dehydration-mediated pDADMAC layer contraction, the process should be reversible upon rehydration of the devices. To illustrate this, as seen in FIG. 4, we introduced our device to a humidity chamber, which allowed for atmospheric temperature and humidity to be controlled and maintained.

The device was connected to a string, which was extended out of the chamber top. Initially, under low humidity, the device was fully closed, as seen in FIG. 4 but opened up after the humidity of the environment was increased to 80%. The open arm was then lowered to a box that was in the chamber, and the humidity subsequently decreased to 10%. After this decrease, and waiting (~2.5 h), the device curled back up, but in this case it clamped onto the box. To illustrate the strength of the clamping, the box was lifted off the chamber's bottom surface. Finally, the humidity was increased 70%, which caused the device to open again, dropping the box. We point out here that the box was 4.8 g, while the polymer-based device was only 0.2 g. That is, the box was 24 times the mass of the device.

Figure 5:
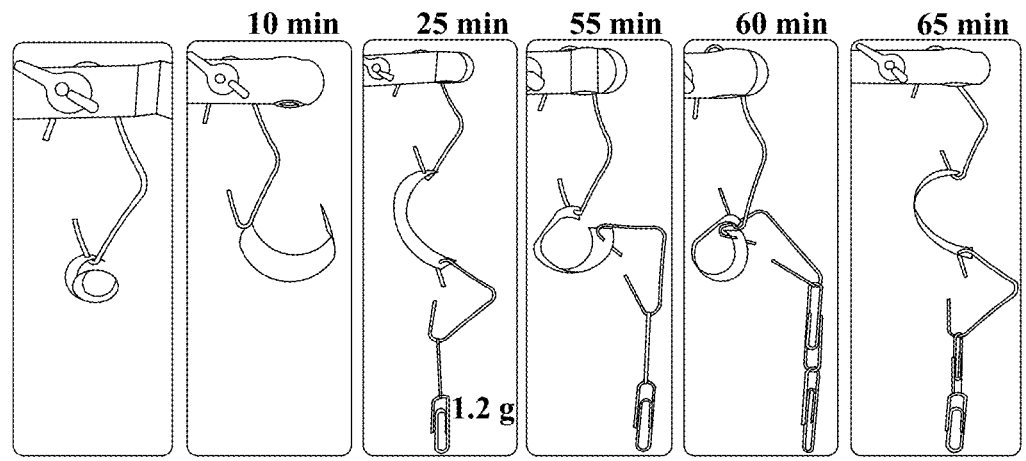
FIG. 5 shows use of the polymer-based devices as artificial muscles. Here, a small curled substrate was hanged from an arm and cycled between low and high humidity. In this case, the device was able to recontract, and curl up with a mass of 1.2 g.

We further studied whether the device can be used as artificial muscle to lift weight and release in response to humidity. To do this we loaded paper clips onto a curled substrate and exposed the set up to a humid environment. This is depicted in FIG. 5. In each case, paperclips (used as weights) were hung off the end of the device or not, the device opened up upon increasing the humidity and curled back up when the humidity was decreased. This is similar to an arm curling a mass, but in this case, the mass that is being lifted is 14 times the mass of the device. Given that a human arm is ~6.5% of the total mass of the human body, this is equivalent to a 150 lb human with a single arm that is capable of lifting 136.5 lbs.

Figure 6:
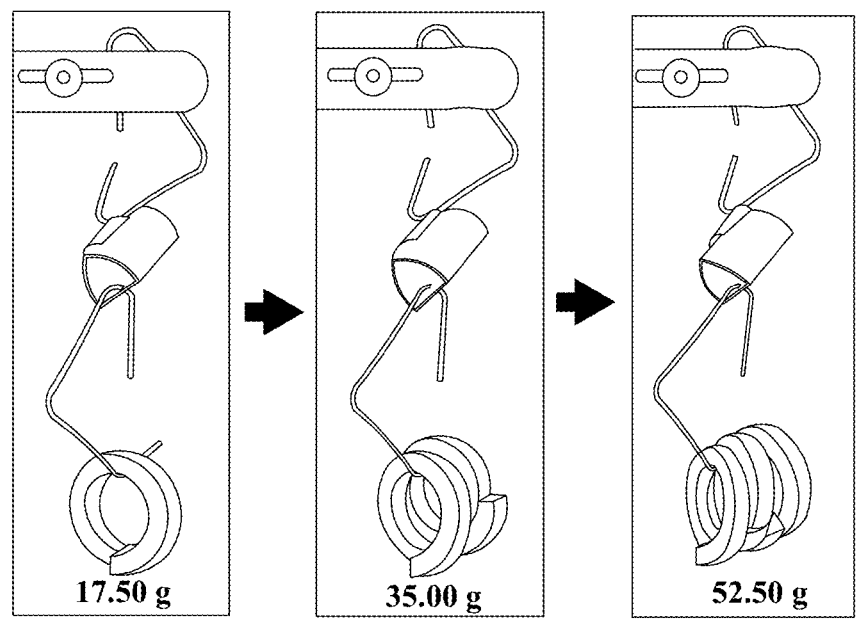
FIG. 6 shows a dry polymer-based device resisting uncurling as masses are hung from the end of the device.

Finally, we showed that dried substrates could resist opening when a force is applied to them. This is illustrated in FIG. 6, where weights were hung from the end of a suspended device showing that even with 52.50 g hanging from the end of the dried device it is not significantly unwound. Using the same numbers as above for the mass of a human arm, this is equivalent to a 150 lb human that has an arm capable of resisting a force of 2560 lbs pulling on the arm.

In conclusion, we find that polyelectrolyte mediated crosslinking of microgels painted on Au coated substrates are able to actuate, and act as "muscles" or "arms" in response to humidity. These arms are able to lift relatively large masses, and resist forces many times their own mass. Given this, we strongly believe that this device can be further developed to optimize its capability as artificial arm. This study is very promising to realize responsive polymer based materials for application in soft-robotics and artificial muscles.

Experimental Section

Microgel Synthesis:

Microgels composed of poly (N-isopropylacrylamide)-co-acrylic acid (pNIPAm-co-AAc) were synthesized via temperature-ramp, surfactant free, free radical precipitation polymerization as described previously.[17-19] The monomer mixture, with a total concentration of 154 mM, was comprised of 85% (mole/mole) NIPAm, 10% AAc, and 5% BIS as the crosslinker. NIPAm (17.0 mmol), and BIS (1.0 mmol) were dissolved in deionized water (100 mL) with stirring in a beaker. The mixture was filtered through a 0.2 μm filter affixed to a 20 mL syringe into a 200 mL 3-neck round-bottom flask. The beaker was rinsed with 25 mL of deionized water and then filtered into the NIPAm/BIS solution. The flask was then equipped with a temperature probe, a condenser and a $N_2$ gas inlet. The solution was bubbled with $N_2$ gas for ~1.5 h, while stirring at a rate of 450 rpm, allowing the temperature to reach 45° C. AAc (2.0 mmol) was then added to the heated mixture with a micropipette in one aliquot. A 0.078 M aqueous solution of APS (5 mL) was delivered to the reaction flask with a transfer pipet to initiate the reaction. Immediately following initiation, a temperature ramp of 45 to 65° C. was applied to the solution at a rate of 30° C./h. The reaction was allowed to proceed overnight at 65° C. After polymerization, the reaction mixture was allowed to cool down to room temperature and filtered through glass wool to remove any large aggregates. The coagulum was rinsed with deionized water and filtered. Aliquots of these microgels (12 mL) were centrifuged at a speed of ~8500 relative centrifugal force (rcf) at 23° C. for ~40 minutes to produce a pellet at the bottom of the centrifuge tube. The supernatant was removed from the pellet of microgels, which was then re-suspended to the original volume (12 mL) using deionized water. This process was repeated until the microgels were cleaned a total of six times to remove any unreacted monomer and/or linear polymer from the microgel solution.

Fabrication of Au Coated Substrate:

Briefly, 25×25 mm pre-cleaned glass coverslips or transparent flexible plastic sheet were rinsed with DI water and ethanol and dried with $N_2$ gas, and 2 nm of Cr followed by 15 nm or 50 nm of Au were thermally evaporated onto them at a rate of ~0.2 Å s$^{-1}$ and ~0.1 Å s$^{-1}$, respectively, using a Torr International Inc. model THEUPG thermal evaporation system (New Windsor, N.Y.). The Cr acts as adhesion layer to hold the Au layer on the glass/plastic. The Au coated glass substrates were annealed at 250° C. for 3 h and then cooled to room temperature prior to use. An aliquot of about 12 mL of previously purified microgel solution was centrifuged for 30 min at 23° C. at ~8500 relative centrifugal force (rcf) to pack the microgels into a pellet at the bottom of the tube. After removal of the supernatant solution, the microgel pellet was vortexed and placed onto a hot plate at 30° C. A previously coated Cr/Au substrate was rinsed with ethanol, dried with $N_2$, and then placed onto hot plate (Corning, N.Y.) set to 30° C. An aliquot (40 μL for each 25×25 mm area) of the concentrated microgels was put onto the substrate and then spread toward each edges using the side of a micropipette tip. The substrate was rotated 90°, and the microgel solution was spread again. The spreading and rotation continued until the microgel solution became too viscous to spread due to drying. The microgel solution was allowed to dry completely on the substrate for 2 h with the hot plate temperature set to 35° C. After 2 h, the dry film was rinsed copiously with DI water to remove any excess microgels not bound directly to the Au. Microgel painted substrate was then placed into a DI water bath and allowed to incubate overnight on a hot plate set to ~30° C. Following this step, the substrate was again rinsed with DI water to further remove any microgels not bound directly to the Au substrate surface. The microgel painted Au coated substrate was dried with $N_2$ gas and used for the experiment.

Bending Experiment:

Au coated microgel painted substrates were placed in a Petri dish. A specific amount (1.5 mL) of pDADMAC solution (20% in water) was spread onto the microgel layer. The whole set up was undisturbed and dried at ambient temperature. After the complete drying of the film, the humidity response was tested either in a humidity chamber or in air. The box load and release experiment was done in a humidity chamber (Rame-Hart Instrument Co., NJ, USA) and the "paper clip" experiment was done in air. In both cases Air-O-Swiss AOS 7145 Cool Mist Ultrasonic humidifier (manufactured by Swiss Pure Air) was used.

[1] A. Lendlein, H. Y. Jiang, O. Junger, R. Langer, *Nature* 2005, 434, 879.
[2] D. J. Beebe, J. S. Moore, J. M. Bauer, Q. Yu, R. H. Liu, C. Devadoss, B-H. Jo, *Nature* 2000, 404, 588.
[3] T. P. Russell, *Science* 2002, 297, 964.
[4] M. Ma, L. Guo, D. G. Anderson, R. Langer, *Science* 2013, 339, 186.
[5] Y. Osada, A. Matsuda, *Nature* 1995, 376, 219.
[6] Z. L. Wu, M. Moshe, J. Greener, H. Therien-Aubin, Z. Nie, E. Sharon, E. Kumacheva, *Nature Communications* 2013, 4, 1586. doi:10.1038/ncomms2549
[7] K. Liu, C. Cheng, Z. Cheng, K. Wang, R. Ramesh, J. Wu, *Nano Letters* 2012, 12, 6302.
[8] X. Zhang, C. L. Pint, M. H. Lee, B. E. Schubert, A. Jamshidi, K. Takei, H. Ko, A. Gillies, R. Bardhan, J. J. Urban, M. Wu, R. Fearing, A. Javey, *Nano Letters* 2011, 11, 3239.
[9] K. Liu, C. Cheng, Z. Cheng, K. Wang, R. Ramesh, J. Wu, *Nano Letters* 2012, 12, 6302.
[10] M. Yamada, M. Kondo, J.-I. Mamiya, Y. Yu, M. Kinoshita, C. J. Barrett, T. Ikeda, *Angew. Chem. Int. Ed.* 2008, 47, 4986.

[11] J. C. Nawroth, H. Lee, A. W. Feinberg, C. M. Ripplinger, M. L. McCain, A. Grosberg, J. O. Dabiri, K. K. Parker, *Nature Biotechnology*, 2012, 30, 792.

[12] Y. Takashima, S. Hatanaka, M. Otsubo, M. Nakahata, T. Kakuta, A. Hashidzume, H. Yamaguchi, A. Harada, *Nature Communications* 2012, 3, 1270.

[13] M. D. Lima, N. Li, M. Jung de Andrade, S. Fang, J. Oh, G. M. Spinks, M. E. Kozlov, C. S. Haines, D. Suh, J. Foroughi, S. J. Kim, Y. Chen, T. Ware, M. K. Shin, L. D. Machado, A. F. Fonseca, J. D. W. Madden, W. E. Voit, D. S. Galvão, R. H. Baughman, *Science* 2012, 338, 928.

[14] C. Wu, S. Zhou, *Macromolecules* 1995, 28, 8381.

[15] C. Wu, X. Wang, *Physical Review Letters* 1998, 80, 4902.

[16] M. J. Serpe, K. A. Yarmey, C. M. Nolan, L. A. Lyon, *Biomacromolecules* 2005, 6, 408.

[17] M. R. Islam, M. J. Serpe, *Macromolecules* 2013, 46, 1599.

[18] M. R. Islam, M. J. Serpe, *Chem. Commun.* 2013, 49, 2646.

[19] C. D. Sorrell, M. J. Serpe, *Adv. Mater.* 2011, 23, 4088.

In this contribution, we also show that poly (N-isopropylacrylamide) (pNIPAm) microgel-based materials are capable of reversible self-folding into unique 3D structures in an atmosphere of varying humidity. PNIPAm is one of the most well-known and well-studied thermoresponsive polymers. PNIPAm-based macroscopic and colloidal hydrogels (nanogels or microgels, depending on their diameter) are easily synthesized, and have found numerous applications.S18, S19, S20, S21 Furthermore, these materials can be synthesized to respond to additional stimuli other than temperature via copolymerization of various functional monomers (comonomers) at the time of their synthesis.S22, S23 One of the most commonly studied comonomers is acrylic acid (AAc), which has a pKa of approximately 4.25. PNIPAm-co-AAc microgels swell when the solution pH>4.25 due to the deprotonation of AAc increasing the charge-charge repulsion inside the network of microgels. As such, at high pH, the microgels can be considered as polyanions.

Recently, layer-by-layer assembled films of alternating polyanions and polycations have emerged as an important soft materials which showed repeated deformation in response to different stimuli.S22, S24 Polydiallyldimethylammonium chloride (pDADMAC) is a homopolymer of diallyldimethylammonium chloride (DADMAC) and a high charge density cationic polymer (polycation), which has been applied to fabricate various advanced materials by layer-by-layer self-assembly.S25 In the dry state, PDADMAC is also responsive to humidity, exchanging water with the environment and inducing contraction and expansion of the polymer.S5 In this submission we show that by exploiting the individual characteristics of the pNIPAm-co-AAc microgels and the pDADMAC, and their electrostatic interactions, a polymer-based material capable of reversible deformations is achieved. Furthermore, by investigating the self-folding behavior of devices with different dimensions, a mathematical model to predict the behavior was developed. Finally, by using this mathematical model, we could predict the self-folding behavior of the devices, which could then be used to design materials that self-fold into desired three-dimensional structures.

Results and Discussions

Mechanism

Figure 7A:
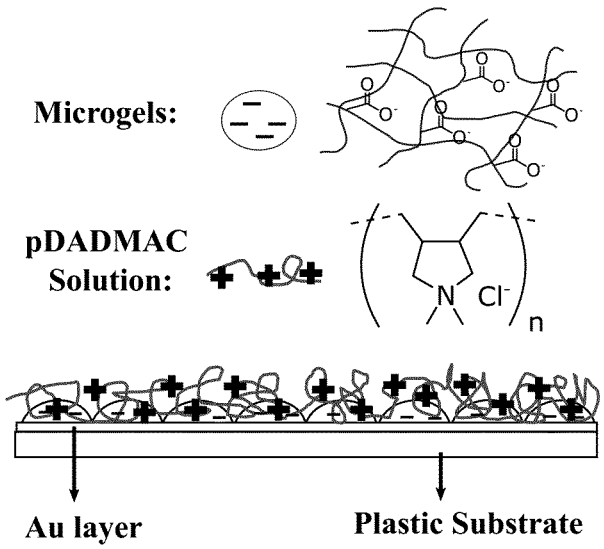
FIG. 7A and FIG. 7B show device construction and self-folding mechanism.
Figure 7B:
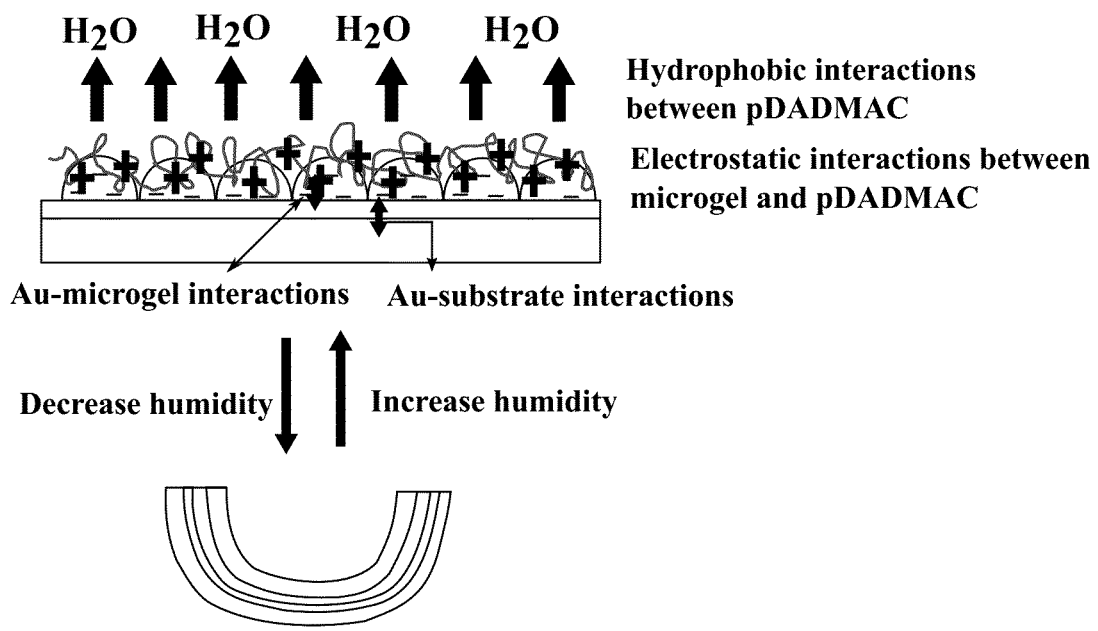

Previously, we designed pNIPAm microgel-pDADMAC-based devices capable of lifting many times their own mass in response to environmental humidity changes.S5 The devices are fabricated by depositing a monolayer of pNIPAm-co-AAc microgels on a Au-coated plastic substrate (FIG. 7A). The apparent solution diameter of the microgels used here was 1548±69 nm (measured using differential interference contrast microscopy). The microgels form a homogenous layer, with a thickness that is ~0.5 of the solution diameter.S21 Subsequently, a specific amount of an aqueous solution of pDADMAC (pH 6.5) was added onto the microgel layer. At this pH, the microgels are negatively charged, while pDADMAC is positively charged. Due to electrostatics, the pDADMAC strongly binds to the microgels, which are strongly bound to the Au substrate. After deposition of the pDADMAC layer, the devices were introduced to a humidity-controlled chamber and allowed to dry at low humidity. Upon drying, the pDADMAC layer contracts due to water evaporation leading to enhanced pDADMAC hydrophobic interactions. As a result of the strong electrostatic interactions between microgels and pDADMAC, together with the strong interactions between gold and microgels, the contraction of the pDADMAC layer causes the device as a whole to deform/bend (FIG. 7B). We point out here that the thickness of microgel-pDADMAC composite is on the scale of mm (measured using calipers).

Figure 8A:
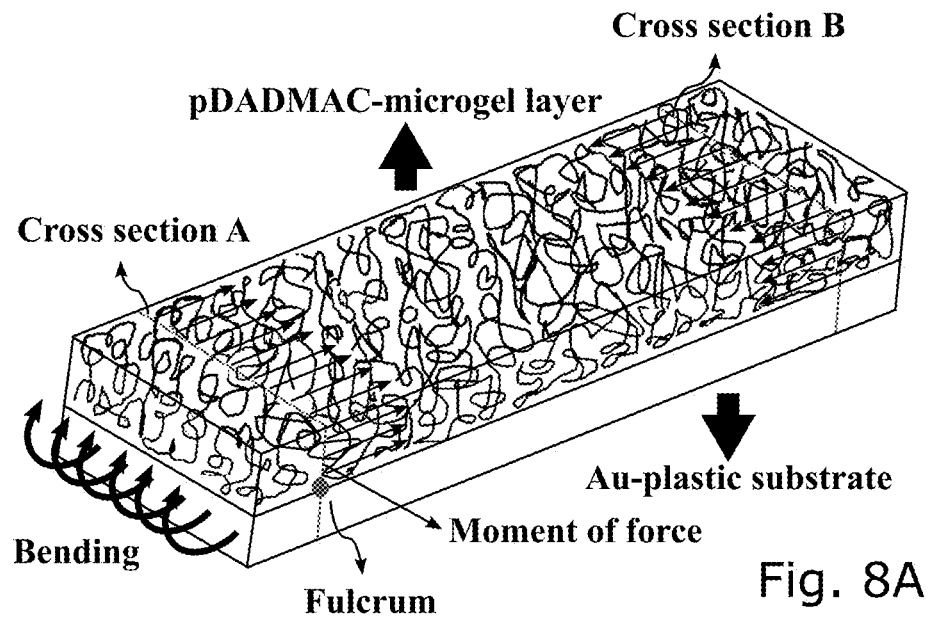
FIG. 8A and FIG. 8B show a Mechanical model used to describe the devices.

To explain how the device bends/deforms, the device can be thought of as two separate layers (FIG. 8A). The pDADMAC-microgel composite (upper layer) serves as the device's active layer, while the Au-plastic substrate (lower layer) is the passive layer. Two assumptions were made in this investigation: (1) the pDADMAC-microgel composite is homogeneous and stress along the layer either linearly increases or decreases; (2) the Au-plastic substrate is not contractible and stress along the layer either linearly increases or decreases. The interface between the two layers can be thought of as being made of an infinite number of points, which do not change location because of assumption (2). Each point is defined as a fulcrum, one of which is shown in FIG. 8A; the two layers are connected at that/those small region(s). In the active layer, we have shown that dehydration leads to contraction, presumably due to enhanced hydrophobic interactions between the pDADMAC.S5 This contraction leads to contracting forces (Fc), which are shown as black vectors in FIG. 8A. The strong forces pull all parts of the Au-plastic lower layer in the direction of force. Meanwhile the lower layer connected to the upper layer by the fulcrum will be pulled in the opposite direction by the torque ($\tau$) generated from the contraction of the upper layer.

Figure 8B:
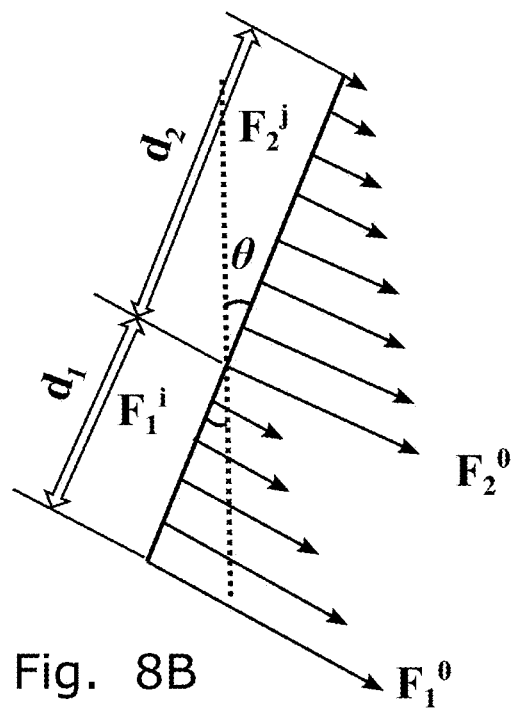

To further explain the bending/folding process and to identify the governing parameters, we developed a mathematical model. To make the model less complex, we concentrated on only a "microscopic" portion of the assembly. As shown in FIG. 8B, the two layers are represented by two lines connected by one fulcrum. The dashed line represents the initial state of the portion of the assembly considered, while the solid line represents the final state after bending is complete. After bending is complete, the force at the fulcrum (at the interface between the pDADMAC and the microgel-Au-plastic layers) is a maximum, which gradually decreases as the distance from this point increases through the upper layer. The forces are noted as F2j indicated by the blue vectors in FIG. 8B. This is the case because we assume that the plastic layer is not contractible (assumption 2), therefore we assume that the interface is likewise not contractible. Therefore, the polymer at the interface has more of a restoring force than the fully contracted polymer layer far away from the interface—much like a spring. F2j in the upper layer depends on three factors: the microscopic bending angle θ, a material related force parameter k2 and the thickness d2 of the upper layer. The fulcrum point shown is common to both layers. Based on the fact that the contraction force in the upper layer is relatively large and that the lower Au-plastic layer isn't contractible (F1i at the interface is 0), we assume that the stress at the fulcrum at the interface is only from the contraction of the upper layer. Then the stress on this point is equal to the remaining contracting force at the bottom of the upper layer and we note it as F20. And the remaining contracting force on the top of the upper layer can be expressed as (F20−k2θd2). Based on assumption 1, the average stress along the upper layer after bending is complete can be expressed as equation (1):

$$F_2^{average} = \frac{(F_2^0 - k_2\theta d_2) + F_2^0}{2} \quad (1)$$

Likewise, the forces on the plastic-Au layer increase as the distance from the interface increases. Again, this can be related to a spring; at the interface where bending is most complete there is little restoring force, while there is still significant forces at the bottom where bending is less complete. These forces are noted as F1i (red vectors), which are in the same direction of the remaining contraction forces in the upper layer, which oppose bending due to the fulcrum. The bending angle θ together with material related force parameter k1 and thickness d1 of the lower layer determines the restoring forces along the lower layer. As shown in FIG. 8B, the stress at the bottom of the lower layer was noted as F10, which can be expressed as (k1θd1). Because the Au-plastic layer is not contractible, the stress on the fulcrum from the bottom layer is 0. Thus, the average stress in this layer can be expressed as equation (2).

$$F_1^{average} = \frac{k_1\theta d_1 + 0}{2} \quad (2)$$

Due to stresses on both layers two torques are formed on both layers separately, which are expressed mathematically below:

$$\tau_1 = F_1^{average} \times r_1 = \frac{k_1\theta d_1 + 0}{2} \times \frac{d_1}{2} \quad (3)$$

$$\tau_2 = F_2^{average} \times r_2 = \frac{(F_2^0 - k_2\theta d_2) + F_2^0}{2} \times \frac{d_2}{2} \quad (4)$$

r represents the distance from the point where the torque is measured to the point where the force is applied in the respective layers, while d is the thickness of the respective layers. In each equation, r is equal to half of the thickness of each layer. At the final state of bending ("equilibrium"), the two torques are equal to maintain a steady bent state, otherwise, the assembly will continue to bend until this is the case. As such, after complete bending equations (3) and (4) are equal leading to equation (5):

$$\frac{k_1\theta d_1 + 0}{2} \times \frac{d_1}{2} = \frac{F_2^0 - k_2\theta d_2 + F_2^0}{2} \times \frac{d_2}{2} \quad (5)$$

Then the microscopic bending angle θ can be expressed as equation (6):

$$\theta = \frac{2d_2 F_2^0}{k_1 d_1^2 + k_2 d_2^2} \quad (6)$$

Again, this is the "microscopic" bending angle, which leads to macroscopic device bending. Macroscopically the device will show specific curvature after bending is complete. Theoretically, we can represent the curvature by the radius (R) of rolls or incomplete rolls after bending. In this case, microscopically F20 in equation (6) can be expressed as one force (between the upper layer and the lower layer), which is determined by another force parameter, the interfacial force parameter (k) multiplied by a length (L), which represents the length of the interfacial layer exerting forces on the fulcrum on the microscopic level. Furthermore, L can be expressed as the bending angle θ multiplied by (R−d1). Therefore, F20 can be represented by equation (7):

$$F_2^0 = k\theta(R - d_1) \quad (7)$$

Subsequently, equation (6) can be rewritten as equation (8):

$$\theta = \frac{2d_2 k\theta(R - d_1)}{k_1 d_1^2 + k_2 d_2^2} \quad (8)$$

Finally, the macroscopically observed R can be expressed as equation (9):

$$R = \frac{k_1 d_1^2/k + k_2 d_2^2/k}{2d_2} + d_1 \quad (9)$$

As k, k1, k2 are force parameters (constants) determined by the materials themselves, from equation (9) we conclude that the radius after bending is only related to the thickness of each layer d1 and d2.

To test our mathematical model, we fabricated rectangular devices of different dimension, but containing the same upper and lower layer thicknesses. As predicted from equation (9), these devices should self-fold to yield similar values for R. There is a precedent for this result; in a previous study, Li and coworkers S26 observed that the curvature of rolls after bending of rectangular bilayers depended on the thickness of the layers and strain, but not the bilayer dimensions. While this is the case, our investigation is the first to develop and test a mathematical model that is capable of predicting the self-folding behavior of such materials. Furthermore, we investigated how the bending of a single device, with given dimensions, depended on the upper layer thickness (d2) to determine if equation (9) could indeed be used to predict R.

Results

Self-Folding Behavior of Rectangular Devices

Figures 9A, 9B:
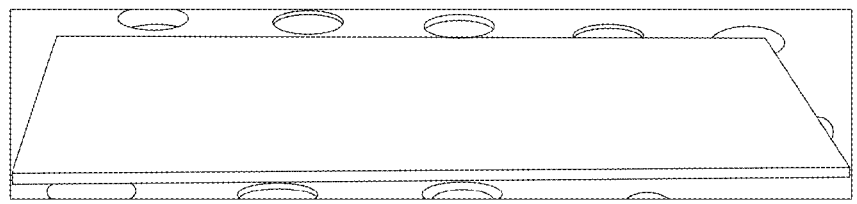
FIG. 9A and FIG. 9B show images of devices before and after bending.
Figure 10:
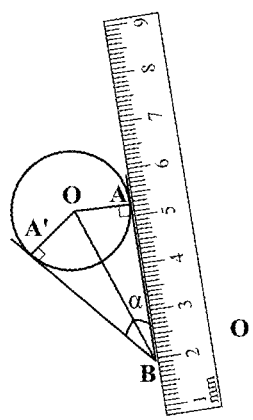
FIG. 10 shows the protocol used for measuring the radius of the devices after bending. AB and A'B are two tangents perpendicular to the radius of a device OA and OA', respectively. B is the intersection of the two tangents. α is the angle between the two tangents. Two rulers were used to measure AB and A'B, while a protractor was used to measure the angle between the rulers to determine α.

Self-folding is a term used to describe materials that transform autonomously from two-dimensional materials into three dimensional structures such as spirals, tubes, corrugated sheets or polyhedron.S27 Self-folding can take place on many length scales—from meters to nanometers.S28, S29 Here, we show that the self-folding behavior of materials with centimeter-scale dimensions can be predicted using equation (9). To accomplish this, we fabricated rectangular devices (see FIGS. 7 and 8) with four different aspect ratios. Furthermore, for each aspect ratio, we fabricated devices of different overall dimensions. In each case, the amount of pDADMAC added to each device was scaled for their individual dimensions such that the amount of pDADMAC on a given device area was the same from device to device. Therefore, the thickness of the upper layer (d2) was constant. Furthermore, the devices were constructed from the same lower layer material, maintaining the same lower layer thickness (d1) from device to device. FIG. 9A is a photograph of a representative device (3 cm×9 cm) with pDADMAC deposited in its unfolded state (high humidity), while FIG. 9B shows the final state of the devices dried under the same conditions. It is interesting to note that the devices tend to self-fold into unique three-dimensional structures after drying, which will be the subject of a future investigation. Here, we were interested in the radius of curvature (R in equation (9)) and how that depended on the device's aspect ratio and size. To measure the radius of curvature, we used the approach shown schematically in FIG. 10. The circle in FIG. 10 represents a device in its final state. If two lines are drawn (AB and A'B), perpendicular to the radii (OA and OA') they intersect at point B. As a result, two triangles are formed. In Δ OAB, the length AB can be measured using two rulers placed on the tangents to the curvature of the device—the "length" at the intersection point is AB. Furthermore, the angle between the two rulers at that condition is also measured. With this information, the radius OA could be determined using equation (10) and equation (11):

$$\tan\frac{\alpha}{2} = \frac{OA}{AB} \quad (10)$$

$$OA = AB \times \tan\frac{\alpha}{2} \quad (11)$$

For each device, we measured the radius at 5 different locations at a humidity of 19.7% and temperature of 23° C. and plotted the average radius as a function of the area (length×width) for each aspect ratio. The data is shown in FIG. 11A to FIG. 11D. As can be seen, while the individual devices may self-fold into different structures (tubes/spirals), the radius of curvature for all the devices, regardless of overall size or aspect ratio, is in the range of 0.75~0.85 cm. From these results, we conclude that the final radius of the devices only depends on the thickness of the two layers. Again, investigations into the self-folding into different structures will be the subject of a future publication.

Figure 12:
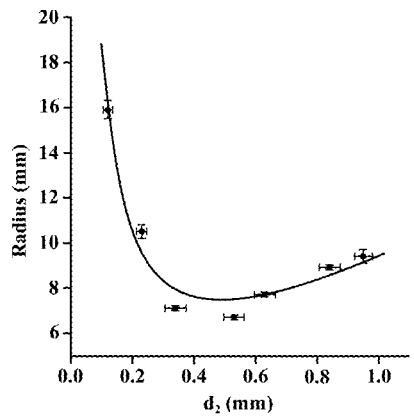
FIG. 12 shows dependence of device radius on pDADMAC layer thickness. The data points are real data obtained by measuring the radius of two separate devices with a given $d_2$. Each point is the average of 10 radii determined at 5 different locations of the two separate devices. The error bars are the standard deviations of the measured $d_2$ and radius. The blue curve is the best fit of equation (12) to the data yielding values for A and B of 3.6±0.4 and 15.1±2.4, respectively. The equation was fit to the data using Matlab software.
Figure 11A:
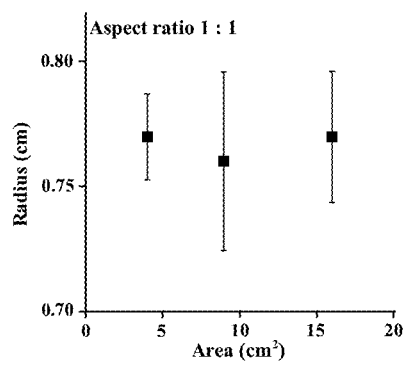
FIG. 11A to FIG. 11D shows the measured radius of the devices as a function of their size and aspect ratio. As can be seen, the measured radius of the devices didn't depend strongly on their size and aspect ratio. Three devices were made at each size and aspect ratio and the radius determined at 5 different locations for each device. Each point is therefore the average of 15 radius values measured from 3 devices at 5 different locations. The error bars indicate the standard deviation.
Figure 11B:
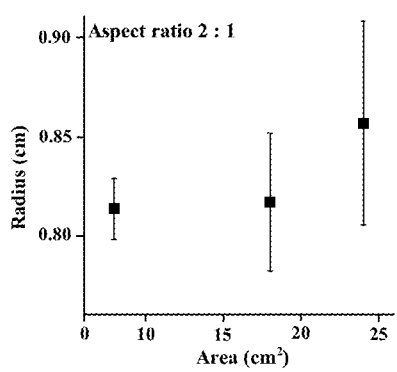
Figure 11C:
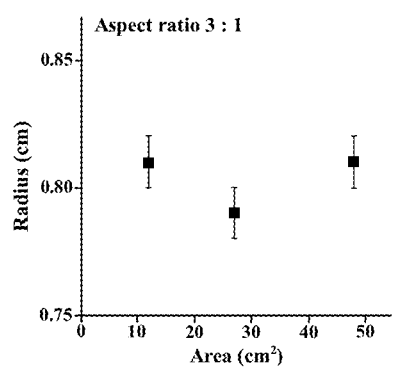
Figure 11D:
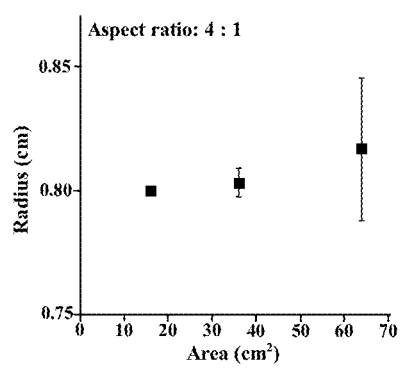
Figure 13A:
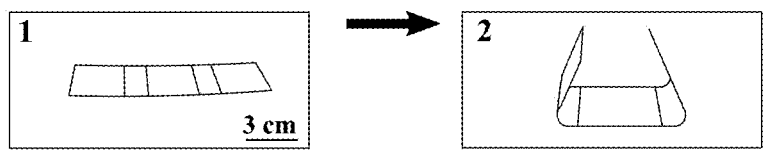
FIG. 13A to 13G, each consisting of plates 1 and 2, show rationally designed devices capable of self-folding into three-dimensional structures. Column 1) Specially designed microgel coated Au/plastic substrates with a given width of pDADMAC deposited at specific locations (red outlined areas) to yield the desired 3D structure Column 2) after drying. For devices a, b, c, and d the width of the pDADMAC solution deposited in each red frame was around ~1.25 cm. For device e, the width of the pDADMAC solution was ~2 cm. For devices f and g both sides of the plastic substrates were coated with Au and microgels, and pDADMAC subsequently deposited on specific locations with a width of ~1.25 cm.
Figure 13B:
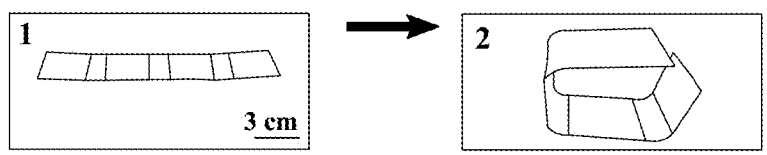
Figure 13C:
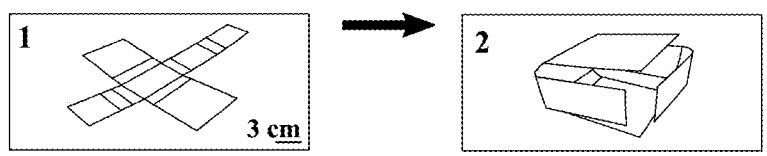
Figure 13D:
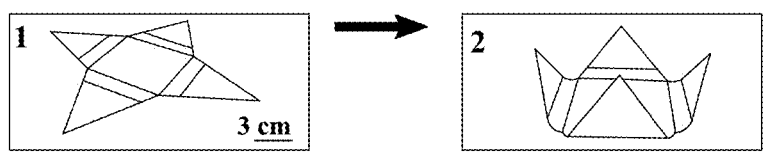
Figure 13E:
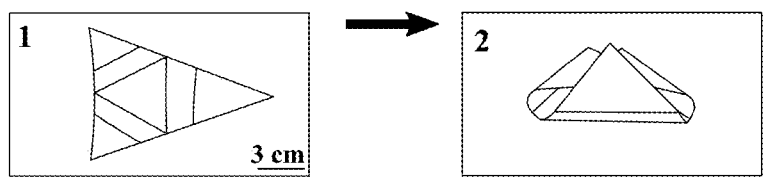
Figure 13F:
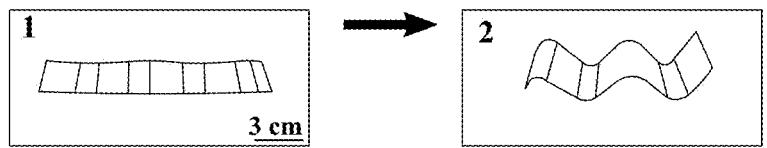
Figure 13G:
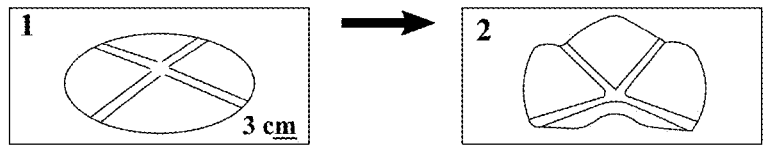

In addition, using devices with dimensions of 9 cm×3 cm, the thickness of the upper layer d2 was systematically varied by depositing different amounts of pDADMAC solution on the surface of the microgel-Au-plastic substrate. In this case, the thickness of Au-plastic substrate was kept constant. The volumes of pDADMAC used were 1-10 mL, which yielded a range of d2 (see Electronic Supporting Information), and two devices of each thickness were prepared for each volume. Following drying of the pDADMAC layer, its thickness was measured using a digital caliper and the radius of curvature was measured for each device using the same protocol as above. The data is plotted in FIG. 12. As can be seen, the radius of curvature depends dramatically on the thickness of the upper layer. Subsequently, by knowing the thicknesses of both layers, we could fit equation (12) to the data in FIG. 12, and the best fit values for A and B determined. It should be pointed out here that equation (12) is the same as equation (9) with the constants A and B representing the individual k-containing terms in equation (9). As a result of the fit, the best fit values for A and B in equation (12) were found to be 3.6±0.4 and 15.1±2.4, respectively.

$$R = \frac{A + Bd_2^2}{2d_2} + 0.1016 \quad (12)$$

Further, we tested the model by fabricating device with given d2 and comparing the predicted and measured R values. For d2 of 0.45 mm, and 0.72 mm, the model predicts an R of 7.40 mm and 8.02 mm. This is in comparison to the measured values of 6.63 mm and 8.43 mm, as can be seen the model closely predicts the experimental R.

Controlling the Self-Folding Process

Using our mechanical and mathematical models above to predict important design parameters, we created materials that are capable of self-folding into desired 3D structures. To accomplish this, an empirical rule was developed to calculate the amount of pDADMAC-microgel composite needed to be added to the Au-plastic substrate to make the whole device self-fold by a specific angle α. Equation (13) was developed to predict this behavior:

$$\widehat{AA}' = \frac{180° - \alpha}{360°} \times 2\pi \times OA \quad (13)$$

Wherein, $\widehat{AA}$ is the length of the arc AA' in FIG. 10, while OA is the radius of the self-folded structure at a specific humidity and temperature. 2π×OA is the circumference of the self-folded device. For example, at humidity of 19.7% (dry) and temperature of 23° C., if we want a structure with a curling angle α of 90°, we need the length of $\widehat{AA}$ to be ~1.25 cm according to the equation (13). That means, if we want the device to bend to yield a right angle, we need to deposit a layer of pDADMAC onto the device with a width of ~1.25 cm along the direction of bending. The volume of pDADMAC added to the device should yield the same d2 as used above. Following this rule, we designed devices capable of self-folding into discrete and predetermined 3D structures. As can be seen in FIG. 13, the width and direction of the deposited pDADMAC layer depends on how we want the device to self-fold, and through this, we have great control over the device's self-folding behavior.

Conclusion

In summary, we investigated in detail the self-folding behavior of rectangular humidity-responsive microgel-based polymer composites deposited on a substrate of varying dimensions and aspect ratios. We detailed a mechanical and mathematical model that is capable of describing the self-folding characteristics of these bilayer devices. Furthermore, using this information, we were able to devise an approach for fabricating devices that self-fold into predetermined 3D structures with varying complexities. We hypothesize that the material parameters defined in the presented model is one that can be generalized to essentially any bilayer material, and similar studies can be completed. This work paves the way for producing stimuli responsive adaptive polymer materials, which have potential applications in actuation, sensing, artificial muscles and robotics.

Acknowledgments

MJS acknowledges funding from the University of Alberta (the Department of Chemistry and the Faculty of Science), the Natural Science and Engineering Research Council (NSERC), the Canada Foundation for Innovation (CFI), the Alberta Advanced Education & Technology Small Equipment Grants Program (AET/SEGP) and Grand Challenges Canada. MJS acknowledges Mark McDermott for the use of the thermal evaporator.

EXPERIMENTAL

Materials: N-isopropylacrylamide was purchased from TCI (Portland, Oreg.) and purified by recrystallization from hexanes (ACS reagent grade, EMD, Gibbstown, N.J.) prior to use. N, N-methylenebisacrylamide (BIS) (99%), acrylic acid (AAc) (99%), and ammonium persulfate (APS) (98+%) were obtained from Sigma-Aldrich (Oakville, Ontario) and were used as received. Poly (diallyldimethylammonium chloride) solution, pDADMAC of MW<100,000 (20% in water) were purchased from Sigma-Aldrich (St. Louis, Mo.). Deionized (DI) water with a resistivity of 18.2 MΩ·cm was used. Cr/Au annealing was done in a Thermolyne muffle furnace from Thermo Fisher Scientific (Ottawa, Ontario) Anhydrous ethanol was obtained from Commercial Alcohols (Brampton, Ontario). Fisher's finest glass coverslips were 25×25 mm and obtained from Fisher Scientific (Ottawa, Ontario). Cr was 99.999% and obtained from ESPI (Ashland, Oreg.), while Au was 99.99% and obtained from MRCS Canada (Edmonton, AB).

Microgel Synthesis: Microgels composed of poly (N-isopropylacrylamide)-co-acrylic acid (pNIPAm-co-AAc) were synthesized via radical precipitation polymerization as described previously.S21 The monomer mixture, with a total concentration of 154 mM, was comprised of 85% (mole/mole) NIPAm, 10% AAc, and 5% BIS as the crosslinker. NIPAm (17.0 mmol), and BIS (1.0 mmol) were dissolved in deionized water (100 mL) with stirring in a beaker. The mixture was filtered through a 0.2 µm filter affixed to a 20 mL syringe into a 200 mL 3-neck round-bottom flask. The beaker was rinsed with 25 mL of deionized water and then filtered into the NIPAm/BIS solution. The flask was then equipped with a temperature probe, a condenser and a N2 gas inlet. The solution was bubbled with N2 gas for ~1.5 h, while stirring at a rate of 450 rpm, allowing the temperature to reach 45° C. AAc (2.0 mmol) was then added to the heated mixture with a micropipette in one aliquot. A 0.078 M aqueous solution of APS (5 mL) was delivered to the reaction flask with a transfer pipet to initiate the reaction. Immediately following initiation, a temperature ramp of 45 to 65° C. was applied to the solution at a rate of 30° C./h. The reaction was allowed to proceed overnight at 65° C. After polymerization, the reaction mixture was allowed to cool down to room temperature and filtered through glass wool to remove any large aggregates. The coagulum was rinsed with deionized water and filtered. Aliquots of these microgels (12 mL) were centrifuged at a speed of ~8500 relative centrifugal force (rcf) at 23° C. for ~40 minutes to produce a pellet at the bottom of the centrifuge tube. The supernatant was removed from the pellet of microgels, which was then re-suspended to the original volume (12 mL) using deionized water. This process was repeated until the microgels were cleaned Fabrication of plastic substrates: Transparent flexible plastic sheets (transparency films for high temperature laser copiers from 3M company, Canada) were rinsed with DI water and ethanol and dried with N2 gas, and 2 nm of Cr followed by 50 nm of Au were thermally evaporated onto them at a rate of ~0.2 Å s−1 and ~0.1 Å s−1, respectively, using a Torr International Inc. model THEUPG thermal evaporation system (New Windsor, N.Y.). The Cr acts as adhesion layer to hold the Au layer on the plastic. An aliquot of about 12 mL of previously purified microgel solution was centrifuged for 30 min at 23° C. at ~8500 relative centrifugal force (rcf) to pack the microgels into a pellet at the bottom of the tube. After removal of the supernatant solution, the microgel pellet was vortexed and placed onto a hot plate at 30° C. A previously coated Cr/Au substrate was rinsed with ethanol, dried with N2, and then placed onto hot plate (Corning, N.Y.) set to 30° C. Aliquots (40 µL for each 25×25 mm area) of the concentrated microgels were put onto the substrate and then spread toward each edges using the side of a micropipette tip, as previously described.S30 The microgel solution was allowed to dry completely on the substrate for 2 h with the hot plate temperature set to 35° C. After 2 h, the dry film was rinsed copiously to remove any unreacted monomer and/or linear polymer from the microgel solution. Then the substrates were washed copiously with DI water to remove any excess microgels not bound directly to the Au. Microgel painted substrate was then placed into a DI water bath and allowed to incubate overnight on a hot plate set to ~30° C. Following this step, the substrate was again rinsed with DI water to further remove any microgels not bound directly to the Au substrate surface. The microgel painted Au coated substrate was dried with N2 gas and used for the experiment.

Self-folding devices: A specific amount of pDADMAC solution (pH 6.5, 20 wt % in water) was spread onto the microgel layer. The whole set up was undisturbed and dried at ambient temperature/humidity. After the complete drying of the film, the devices were moved into the chamber, which can control the environmental humidity. Air-O-Swiss AOS 7145 Cool Mist Ultrasonic humidifier (manufactured by Swiss Pure Air) was used to control the humidity in the chamber with an electronic feedback mechanism to maintain a steady humidity.

Various techniques may be used to transform the degree of response of the microgel to a stimulus, for example humidity, into a measurement. Any of the disclosed stimulus responsive devices may be used. The method comprises subjecting the stimulus responsive device to a stimulus to cause a response of the stimulus responsive device; and converting the response to a detectable signal.

Various methods may be used to convert the response (degree of curl) of the microgel in response to a stimulus to a detectable signal. For example measuring the degree of curl could include sighting a point on the device against a scale, attaching a pointer to the device with the pointer placed against a scale, and reading the location of a part of the device with a laser. In one embodiment, curling of the microgel in response to a stimulus, for example humidity, may raise or lower a series of weights off or onto a weigh scale, and the change of weight may show the degree of curl.

In another embodiment, the porous microgel may be combined with a strain sensor for use as a sensor. In some embodiments, a metal layer, for example gold, with or without a supporting substrate depending on the application, may be attached directly to or deposited on a bilayer structure as disclosed or the flexible substrate.

Figure 14:
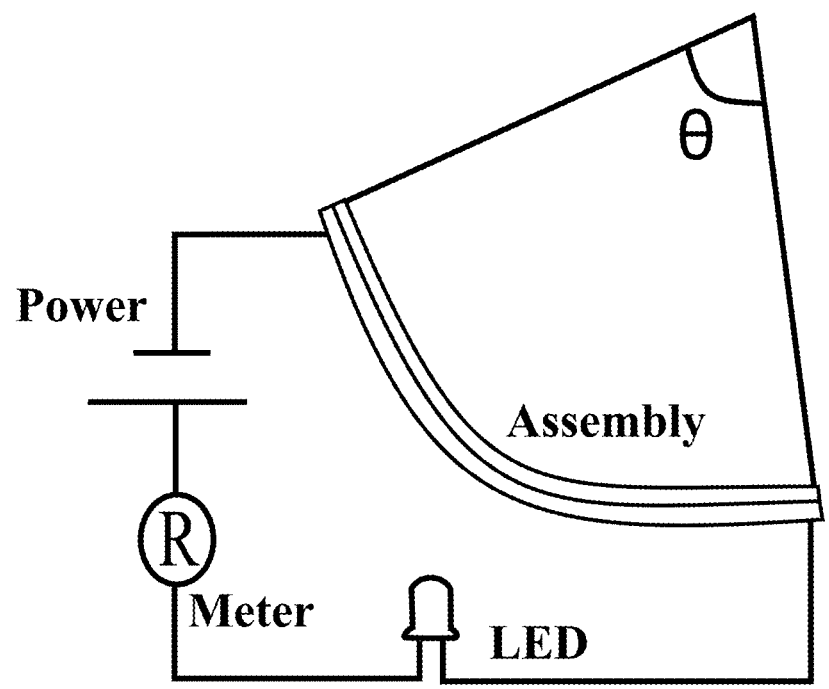
FIG. 14 shows a schematic of a device in which the microgel is attached to a metal layer that acts as a strain sensor. Bending of the strain sensor by the microgel with varying amounts of humidity affect the resistivity of the metal layer, which may be detected as for example using the LED shown.

In another embodiment, the metal layer of the strain sensor may be supported by for example a PDMS substrate. In one embodiment for making a Au/PDMS hybrid structured strain sensor, a 0.5 mm thick PDMS elastomeric substrate may be prepared by mixing a silicone gel and crosslinker in a 10:1 volume ratio and curing them for overnight at 70° C. on a plastic substrate. Successive depositions of 2 nm adhesion layers of chromium and 50 nm gold on the full surface of PDMS without other treatments may be performed by metal thermal evaporation. The resulting strain sensor is a mechanically bendable and stretchable device made of metal nanoparticles interconnected with each other. The strain sensor so prepared may be combined with one of the disclosed bilayer devices, for example by attaching the PDMS surface of the strain sensor directly on the plastic surface (substrate) of the device. In this example, Van der Waals forces between these two surfaces provides the major source of bonding. In a circuit made by connecting the assembly with one power supply and one resistance measurement meter/LED light, as shown in FIG. 14, the device acts as a humidity sensor. At high humidity level of 45%, the assembly is flat. In this condition, the resistance from the strain sensor is relatively low. When the humidity is set to 35%, due to the loss of water of pDADMAC layer, the assembly bends to a small degree, which induces stretching of the strain sensor at the bottom and increases resistance by increasing the electrical percolation length in the gold film. Resistance shows relatively linear changes with change in humidity, with the assembly serving as a very reversible and repeatable humidity sensing device. Strain sensors made by depositing thin good conductive metal films, other than carbon nanotubes or graphene, used with the bilayer device may be used in controlling system (actuators). In a simple example, by adding an LED light in the circuit, the change of humidity can control the light intensity of the LED. In an embodiment, the assembly comprised layers of Au-PDMS-Plastic-Au-microgels-pDADMAC. In this example, Au-PDMS is fabricated separately from the rest of the layers, and the layers are physically coupled together, but other methods and layer orders may be used.

REFERENCES

S1. Stoychev, G., Turcaud, S., Dunlop, J. W. C. & Ionov, L. Hierarchical multi-step folding of polymer bilayers. Adv. Funct. Mater. 23, 2295-2300 (2013).

S2. Fuhrer, R., Athanassiou, E. K., Luechinger, N. A. & Stark, W. J. Crosslinking metal nanoparticles into the polymer backbone of hydrogels enables preparation of soft, magnetic field-driven actuators with muscle-like flexibility. Small 5, 383-388 (2009).

S3. Liu, K. et al. Giant-amplitude, high-work density microactuators with phase transition activated nanolayer bimorphs. Nano Lett. 12, 6302-6308 (2012).

S4. Alben, S., Balakrisnan, B. & Smela, E. Edge effects determine the direction of bilayer bending. Nano Lett. 11, 2280-2285 (2011).

S5. Islam, M. R., Li, X., Smyth, K. & Serpe, M. J. Polymer-based muscle expansion and contraction. Angew. Chem. Int. Ed. 52, 10330-10333 (2013).

S6. Yakacki, C. M., Satarkar, N. S., Gall, K., Likos, R. & Hilt, J. Z. Shape-memory polymer networks with fe3o4 nanoparticles for remote activation. J. Appl. Polym. Sci. 112, 3166-3176 (2009).

S7. Fukushima, T., Asaka, K., Kosaka, A. & Aida, T. Fully plastic actuator through layer-by-layer casting with ionic-liquid-based bucky gel. Angew. Chem. Int. Ed. 117, 2462-2465 (2005).

S8. Ahir, S. V. & Terentjev, E. M. Photomechanical actuation in polymer-nanotube composites. Nat. Mater. 4, 491-495 (2005).

S9. Yoshida, R. et al. Comb-type grafted hydrogels with rapid deswelling response to temperature changes. Nature 374, 240-242 (1995).

S10. Kopecek, J. Polymer chemistry: Swell gels. Nature 417, 388-391 (2002).

S11. Hu, Z., Zhang, X. & Li, Y. Synthesis and application of modulated polymer gels. Science 269, 525-527 (1995).

S12. Kim, J., Hanna, J. A., Byun, M., Santangelo, C. D. & Hayward, R. C. Designing responsive buckled surfaces by halftone gel lithography. Science 335, 1201-1205 (2012).

S13. Thérien-Aubin, H., Wu, Z. L., Nie, Z. & Kumacheva, E. Multiple shape transformations of composite hydrogel sheets. J. Am. Chem. Soc. 135, 4834-4839 (2013).

S14. Wang, E., Desai, M. S. & Lee, S.-W. Light-controlled graphene-elastin composite hydrogel actuators. Nano Lett. 13, 2826-2830 (2013).

S15. Kumpfer, J. R. & Rowan, S. J. Thermo-, photo-, and chemo-responsive shape-memory properties from photo-cross-linked metallo-supramolecular polymers. J. Am. Chem. Soc. 133, 12866-12874 (2011).

S16. Ma, M., Guo, L., Anderson, D. G. & Langer, R. Bio-inspired polymer composite actuator and generator driven by water gradients. Science 339, 186-189 (2013).

S17. Ma, Y. et al. Polyelectrolyte multilayer films for building energetic walking devices. Angew. Chem. Int. Ed. 50, 6254-6257 (2011).

S18. Wu, C. & Zhou, S. Laser light scattering study of the phase transition of poly(n-isopropylacrylamide) in water. 1. Single chain. Macromolecules 28, 8381-8387 (1995).

S19. Kawaguchi, H., Fujimoto, K. & Mizuhara, Y. Hydrogel microspheres iii. Temperature-dependent adsorption of proteins on poly-n-isopropylacrylamide hydrogel microspheres. Colloid Polym. Sci. 270, 53-57 (1992).

S20. Serpe, M. J. & Lyon, L. A. Optical and acoustic studies of ph-dependent swelling in microgel thin films. Chem. Mater. 16, 4373-4380 (2004).

S21. Sorrell, C. D. & Serpe, M. J. Reflection order selectivity of color-tunable poly(n-isopropylacrylamide) microgel based etalons. Adv. Mater. 23, 4088-4092 (2011).

S22. Serpe, M. J., Yarmey, K. A., Nolan, C. M. & Lyon, L. A. Doxorubicin uptake and release from microgel thin films. Biomacromolecules 6, 408-413 (2004).

S23. Islam, M. R. & Serpe, M. J. Penetration of polyelectrolytes into charged poly(n-isopropylacrylamide) microgel layers confined between two surfaces. Macromolecules 46, 1599-1606 (2013).

S24. Jaber, J. A. & Schlenoff, J. B. Polyelectrolyte multilayers with reversible thermal responsivity. Macromolecules 38, 1300-1306 (2005).

S25. Kotov, N. A. et al. Mechanism of and defect formation in the self-assembly of polymeric polycation-montmorillonite ultrathin films. J. Am. Chem. Soc. 119, 6821-6832 (1997).

S26. Chun, I. S., Challa, A., Derickson, B., Hsia, K. J. & Li, X. L. Geometry effect on the strain-induced self-rolling of semiconductor membranes. Nano Lett. 10, 3927-3932 (2010).

S27. Leong, T. G., Zarafshar, A. M. & Gracias, D. H. Three-dimensional fabrication at small size scales. Small 6, 792-806 (2010).

S28. Cho, J.-H., Azam, A. & Gracias, D. H. Three dimensional nanofabrication using surface forces†. Langmuir 26, 16534-16539 (2010).

S29. Cho, J.-H. et al. Nanoscale origami for 3d optics. Small 7, 1943-1948 (2011).

S30. Sorrell, C. D., Carter, M. C. D. & Serpe, M. J. A "paint-on" protocol for the *facile* assembly of uniform microgel coatings for color tunable etalon fabrication. ACS Appl. Mater. Interfaces 3, 1140-1147 (2011).

Poly (N-isopropylacrylamide) (pNIPAm) microgel-based materials can be fabricated that self-fold into three-dimensional structures in response to changes in the environmental humidity. The materials are composed of a semi-rigid polymer substrate coated with a thin layer of Au; the Au layer is subsequently coated with a pNIPAm-based microgel layer and finally covered with a solution of polydiallyldimethylammonium chloride (pDADMAC). The pDADMAC layer contracts upon drying causing the material to deform (typically bending); this deformation is completely reversible over many cycles as the environmental humidity is systematically varied. Here, by varying the size and aspect ratio of the polymer substrate, we were able to develop a set of empirical rules that can be applied to predict the material's self-folding behavior. From these rules, we were able to design materials that self-fold from two-dimensional, flat objects into discrete three-dimensional structures, which are fully capable of unfolding and folding multiple times in response to humidity.

Although specific examples of materials and their properties have been disclosed, the range of possible materials that may be used in various embodiments is defined by the claims. For example, materials that may be substituted for pDADMAC include polyallylamine hydrochloride, polyethylene amine and any positively charged polymer that is humidity sensitive.

Other materials may be used for the humidity sensitive material that are sensitive to other stimuli, such as polymers that are sensitive to stimuli such as light, electric field, salinity, pH and magnetic field.

Other materials may be substituted for pNIPAm such as polyhydroxyethyl methacrylate or other porous medium by which the stimulus sensitive material may attach to the substrate and deform upon changes in the stimulus. Various materials may be used instead of the AU, such as Cu, Ni, Al, Ag, and Ti and other metals. Anything elastic may be used for the substrate.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The invention claimed is:

1. A stimulus responsive device comprising:
a flexible substrate;
a porous intermediate layer attached to the flexible substrate; and
a stimulus responsive material bonded to the porous intermediate layer, the stimulus responsive material having a bending state and being responsive to a stimulus to cause a change in the bending state of the stimulus responsive material.

2. The stimulus responsive device of claim 1 in which the flexible substrate comprises a polymer.

3. A stimulus responsive device comprising:
a flexible substrate;
a porous intermediate layer attached to the flexible substrate; and
a stimulus responsive material bonded to the porous intermediate layer, in which the porous intermediate layer comprises a hydrogel.

4. The stimulus responsive device of claim 3 in which the hydrogel comprises pNIPAm or polyhydroxyethyl methacrylate.

5. A stimulus responsive device comprising:
a flexible substrate;
a porous intermediate layer attached to the flexible substrate; and
a stimulus responsive material bonded to the porous intermediate layer, in which the stimulus responsive material is responsive to a change in humidity.

6. The stimulus responsive device of claim 5 in which the stimulus responsive material comprises pDADMAC, polyallylamine hydrochloride, or polyethylene amine.

7. A stimulus responsive device comprising:
a flexible substrate;
a porous intermediate layer attached to the flexible substrate; and
a stimulus responsive material bonded to the porous intermediate layer, further comprising a metal layer between the flexible substrate and the porous intermediate layer.

8. The stimulus responsive device of claim 7 in which the metal layer comprises a first metal adjacent to the flexible substrate and a second metal adjacent to the porous intermediate layer.

9. The stimulus responsive device of claim 8 in which the second metal comprises Au, Cu, Ni, Al, Ag or Ti.

10. The stimulus responsive device of claim 8 in which the first metal comprises Ti or Cr.

11. A stimulus responsive device comprising:
a flexible substrate;
a porous intermediate layer attached to the flexible substrate; and
a stimulus responsive material bonded to the porous intermediate layer, in which the stimulus responsive material is arranged in strips of respective widths, the respective widths chosen to cause bending at the strips of respective specified angles in response to a stimulus.

12. A stimulus responsive device comprising:
a flexible substrate; and
strips of a stimulus responsive material attached to the flexible substrate, in which the strips have respective widths chosen to cause bending at the strips of respective specified angles in response to a stimulus.

13. A method of measuring a stimulus, the method comprising:
subjecting a stimulus responsive device to a stimulus in which the stimulus responsive device comprises
a flexible substrate,
a porous intermediate layer attached to the flexible substrate, and
a stimulus responsive material bonded to the porous intermediate layer, the stimulus responsive material having a bending state and being responsive to a stimulus to cause a change in the bending state of the stimulus responsive material;
wherein the stimulus causes a response of the stimulus responsive device; and
converting the response to a detectable signal.

* * * * *